(12) United States Patent
Larsen et al.

(10) Patent No.: US 6,569,076 B1
(45) Date of Patent: May 27, 2003

(54) RADIOACTIVE SOURCE TRAIN

(75) Inventors: Charles E. Larsen, Cumming, GA (US); Robert C. Farnan, Duluth, GA (US)

(73) Assignee: Novoste Corporation, Norcross, GA (US)

( * ) Notice: Subject to any disclaimer, the term of this patent is extended or adjusted under 35 U.S.C. 154(b) by 0 days.

(21) Appl. No.: 09/616,260

(22) Filed: Jul. 14, 2000

Related U.S. Application Data

(60) Provisional application No. 60/143,730, filed on Jul. 14, 1999.

(51) Int. Cl.$^7$ .............................................. A61M 36/04
(52) U.S. Cl. ......................................................... 600/3
(58) Field of Search .................. 600/1–8; 604/523–524, 604/526–527

(56) References Cited

U.S. PATENT DOCUMENTS

| | | | | |
|---|---|---|---|---|
| 4,763,642 A | * | 8/1988 | Horowitz | 600/7 |
| 4,763,671 A | * | 8/1988 | Goffinet | 600/2 |
| 4,815,449 A | * | 3/1989 | Horowitz | 600/7 |
| 4,819,618 A | | 4/1989 | Liprie | 600/7 |
| 5,141,487 A | | 8/1992 | Liprie | 600/7 |
| 5,199,939 A | | 4/1993 | Dake | 600/3 |
| 5,282,781 A | | 2/1994 | Liprie | 600/3 |
| 5,322,499 A | | 6/1994 | Liprie | 600/8 |
| 5,342,283 A | * | 8/1994 | Good | 600/8 |
| 5,395,300 A | | 3/1995 | Liprie | 600/3 |
| 5,460,592 A | * | 10/1995 | Langton et al. | 600/7 |
| 5,498,227 A | * | 3/1996 | Mawad | 600/3 |
| 5,503,614 A | | 4/1996 | Liprie | 600/7 |
| 5,575,749 A | | 11/1996 | Liprie | 600/3 |
| 5,605,530 A | * | 2/1997 | Fischell et al. | 600/3 |
| 5,618,266 A | | 4/1997 | Liprie | 604/21 |
| 5,624,372 A | | 4/1997 | Liprie | 600/3 |
| 5,683,345 A | * | 11/1997 | Waksman et al. | 600/3 |
| 5,807,231 A | | 9/1998 | Liprie | 600/3 |
| 5,857,956 A | | 1/1999 | Liprie | 600/7 |
| 5,863,284 A | * | 1/1999 | Klein | 600/3 |
| 5,899,882 A | | 5/1999 | Waksman et al. | 604/96 |
| 5,951,458 A | * | 9/1999 | Hastings et al. | 600/3 |
| 6,074,338 A | * | 6/2000 | Popowski et al. | 600/3 |
| 6,074,339 A | * | 6/2000 | Gambale et al. | 600/3 |
| 6,196,963 B1 | * | 3/2001 | Williams | 600/3 |

FOREIGN PATENT DOCUMENTS

DE     1 095 963     12/1960

OTHER PUBLICATIONS

English translation re German patent No. 1 095 963 to Wachmann.

* cited by examiner

*Primary Examiner*—Max F. Hindenburg
*Assistant Examiner*—Joseph A. Cadugan
(74) *Attorney, Agent, or Firm*—Cook, Alex, McFarron, Manzo, Cummings & Mehler, Ltd.

(57) ABSTRACT

A treating element source train that comprises a plurality of treating elements, with each treating element comprising a hollow outer housing closed on each end and a radiation emitting substance encapsulated therein. The treating elements are aligned end-to-end, and a wire is wound around the exterior of the treating elements to maintain the treating elements in their end-to-end relationship. The wire may be helically coiled about the treating elements, or braided around them. Also, the wire may be secured to the proximal and distal treating elements, or to each individual treating element. Preferably, the wire is made of a radiopaque material such as gold, platinum, platinum iridium, tungsten and tantalum. In an alternate embodiment, the source train may be provided with an end cap at either end, with the wire jacket being secured to each endcap.

22 Claims, 7 Drawing Sheets

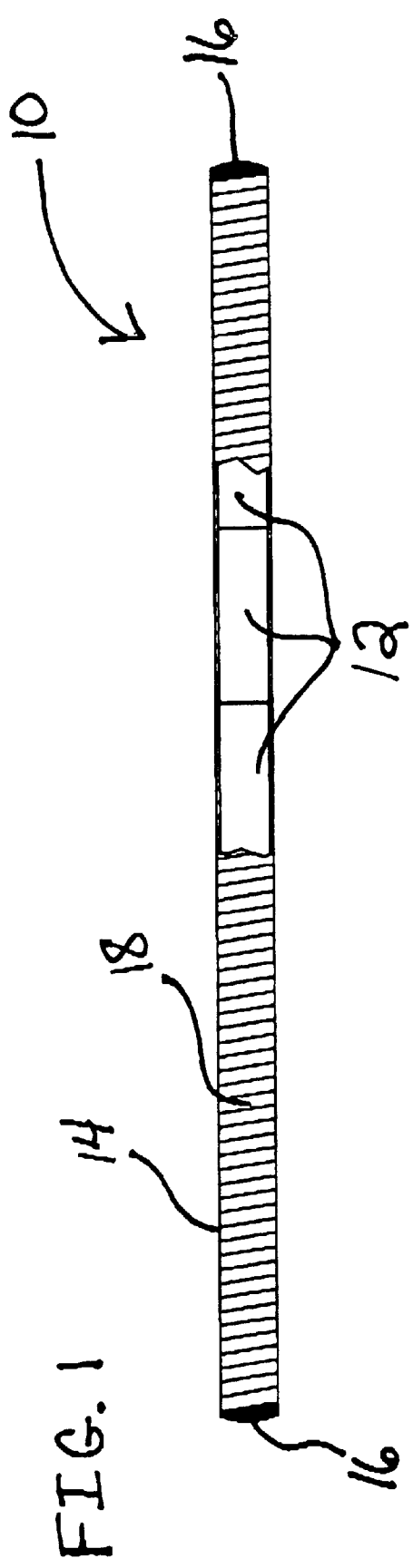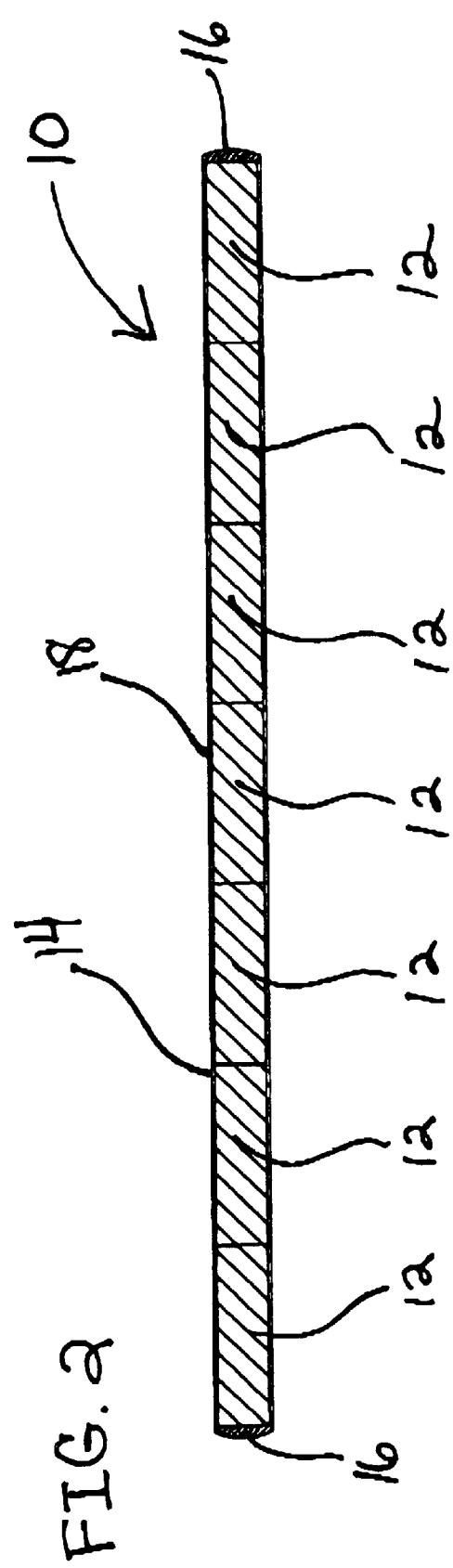

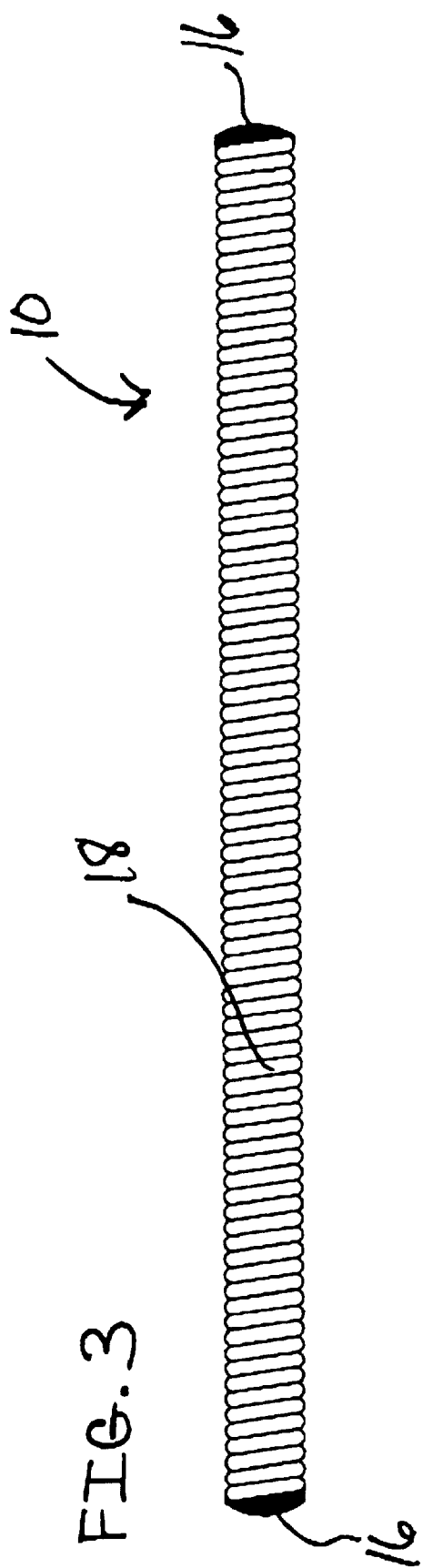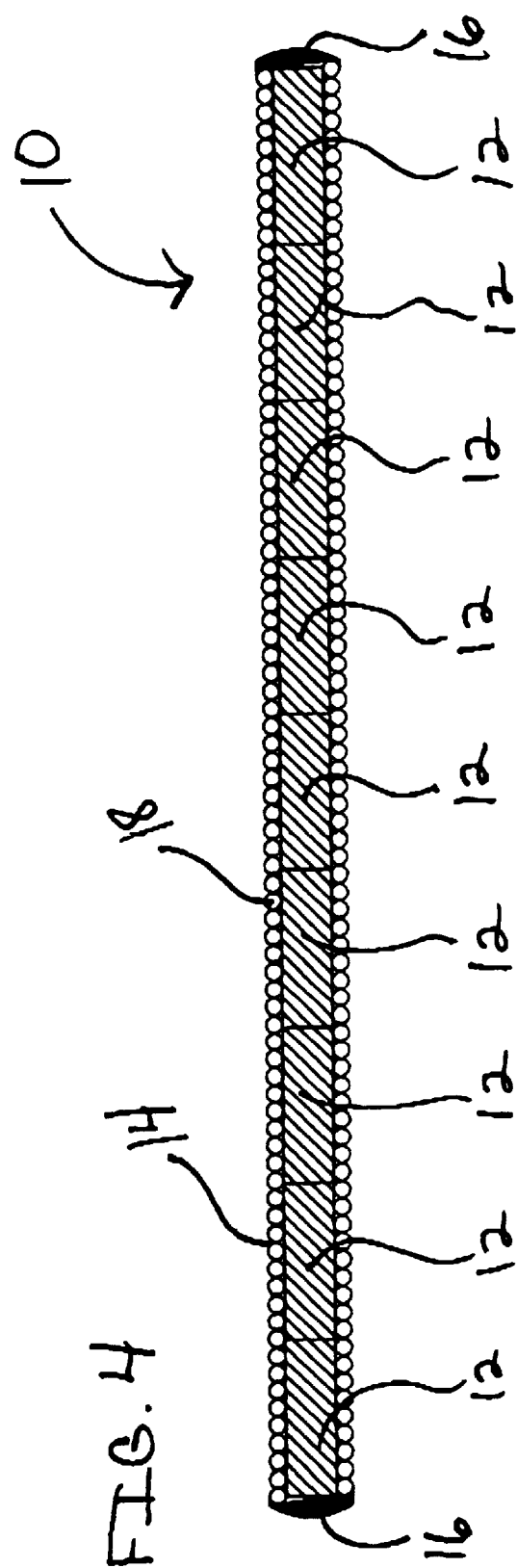

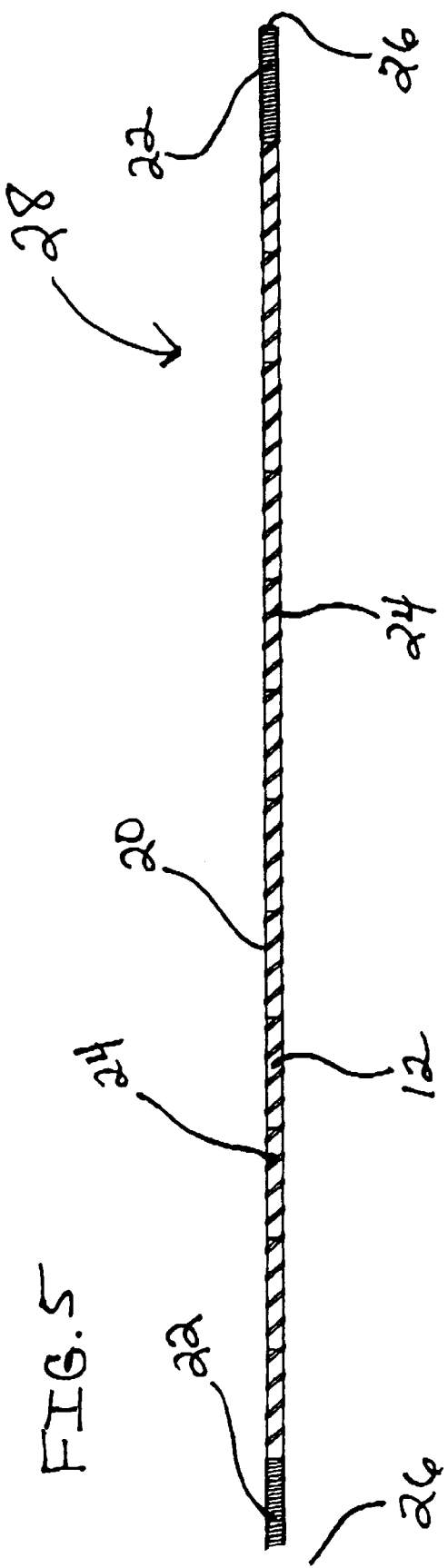

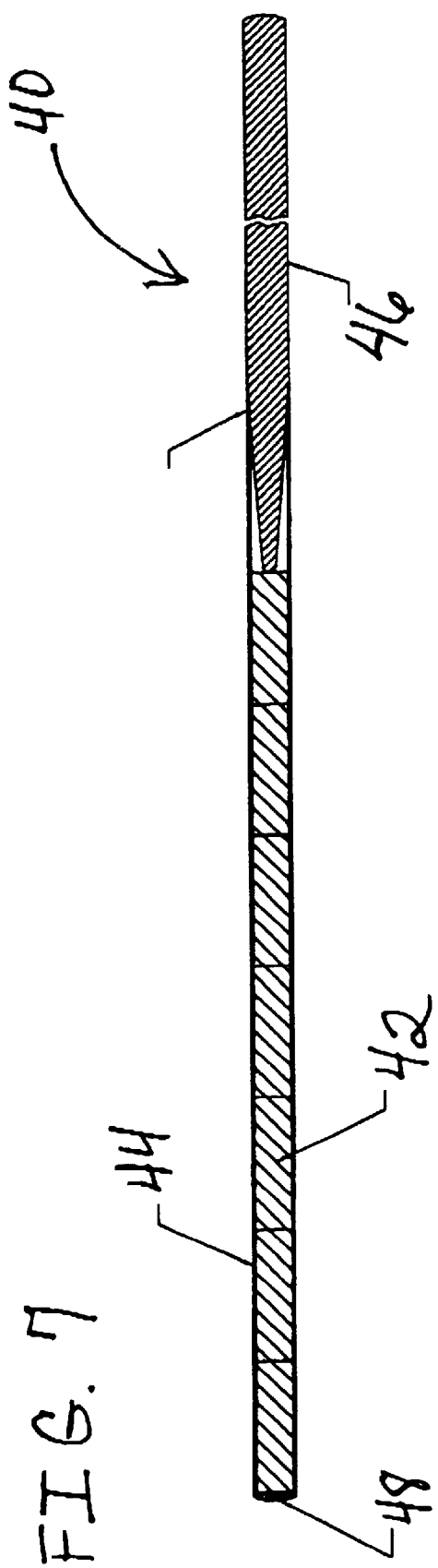

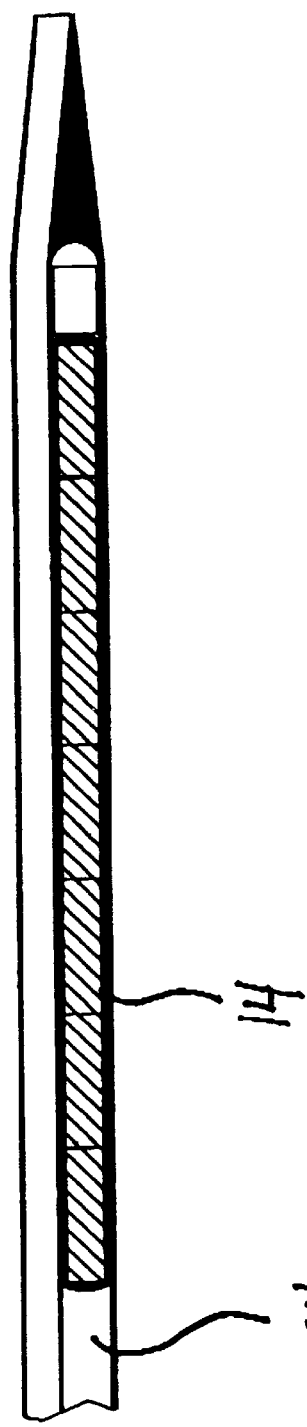
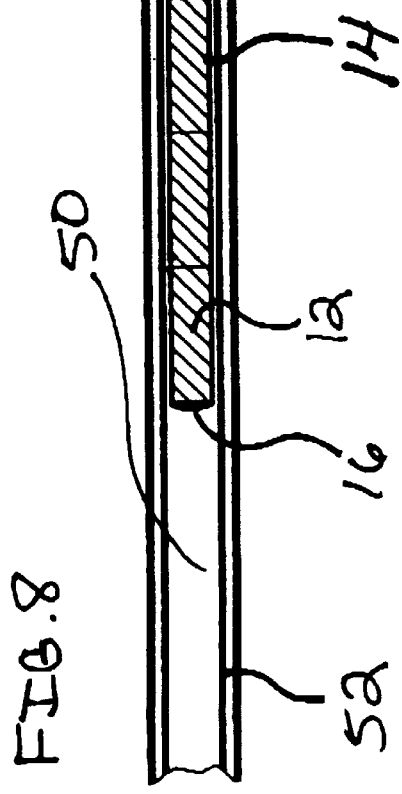
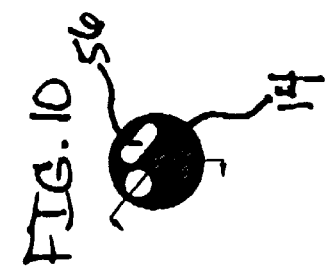

RADIOACTIVE SOURCE TRAIN

CROSS-REFERENCE TO RELATED APPLICATION

This application claims the benefit of U.S. Provisional Application Ser. No. 60/143,730, filed Jul. 14, 1999.

FIELD OF USE

The present invention relates generally to a radioactive source train for medical applications, and more particularly relates to an enclosed or jacketed radioactive source train that acts and moves as one unit as it travels through a catheter or tubular member with one or more lumens for the delivery of radiotherapy within the body of a patient.

BACKGROUND OF THE INVENTION

Intraluminal radiation has been used after angioplasty or atherectomy to treat the affected area of the artery in order to inhibit cell proliferation and, consequently, helped prevent restenosis. Methods and apparatus for such intraluminal radiation treatment are disclosed in U.S. Pat. Nos. 5,899,882 and 6,013,020 and pending applications Ser. Nos. 09/304,752, filed May 4, 1999, Ser. No. 09/469,510, filed Dec. 22, 1999, and Ser. No. 09/522,759, filed Mar. 10, 2000, all of which are incorporated herein by reference. These applications generally disclose apparatus comprising a catheter which is inserted intraluminally into the patient and advanced to the site to be treated. A transfer device is provided for facilitating either the hydraulic or pneumatic advancement and retrieval of individual radioactive treating elements or "seeds" along the catheter to and from the treatment site.

As with any device inserted into the vascular system, it must have sufficient integrity to insure that no pieces or elements are separated from or exit the device into the vascular system. This is particularly true for the treating elements, which are moved to and from the distal end of the catheter. Additionally, because the treating elements are intended to be radioactive, there is a heightened need for safety. Specifically, there is a need to keep track of all of the radioactive treating elements to make sure that all are accounted for. The small size of the treating elements further complicates matters by making visual confirmation of the location of the treating elements more difficult.

Accordingly, it is a principle object of the present invention to provide a treating element source train that keeps the plurality of treating elements together so as to form a single unit.

It is an additional object to provide a source train that is flexible and allows for variable length.

It is a further object of the present invention to provide such a source train system that facilitates the visual confirmation of the location of the source train.

It is a still further object to provide such a source train system that does not interfere with the pattern of radioactive emissions from the treating elements.

SUMMARY OF THE INVENTION

These objects, as well as others which will become apparent upon reference to the following detailed description and drawings are accomplished by a treating element source train that comprises a plurality of treating elements, with each treating element comprising a hollow outer housing closed on each end and a radiation emitting substance encapsulated therein. The treating elements are aligned end-to-end, and one or more wires are wound around the exterior of the treating elements to maintain the treating elements in their end-to-end relationship. The wire may be helically coiled about the treating elements, or braided around them. Also, the wire may be secured to the proximal and distal treating elements, or to each individual treating element. If desired, the wire can be made of a radiopaque material such as gold, platinum, platinum iridium, tungsten, and tantalum.

In an alternate embodiment, the source train may be provided with an end cap at either end, with the wire jacket being secured to each endcap.

DRAWINGS

FIG. 1 shows a first embodiment of the jacket-enclosed radioactive source train of the present invention, with a portion broken-away to reveal the series of radioactive seeds, which are enclosed within the source train jacket.

FIG. 2 shows a longitudinal cross-section of the jacket-enclosed radioactive source train of FIG. 1.

FIG. 3 shows the jacket-enclosed radioactive source train of FIG. 1 formed of round wire in place of flat or ribbon wire, as shown in FIG. 1.

FIG. 4 shows a longitudinal cross-section of the jacket-enclosed radioactive source train of FIG. 3.

FIG. 5 shows the jacket-enclosed radioactive source train in FIG. 1 having variable coil pitch along its length.

FIG. 7 shows the jacket-enclosed radioactive source train of FIG. 1 attached to an elongated push rod.

FIG. 8 shows a longitudinal cross-section of the jacket enclosed radioactive source train of FIG. 1 within the distal end of a co-axial catheter lumen.

FIG. 9 shows a longitudinal cross-section of the jacket-enclosed radioactive source train of FIG. 1 within the distal end of a multi-lumen catheter.

FIG. 10 is an end view of the cross-section of the radioactive source train shown in FIG. 9.

DETAILED DESCRIPTION

Figure 6:
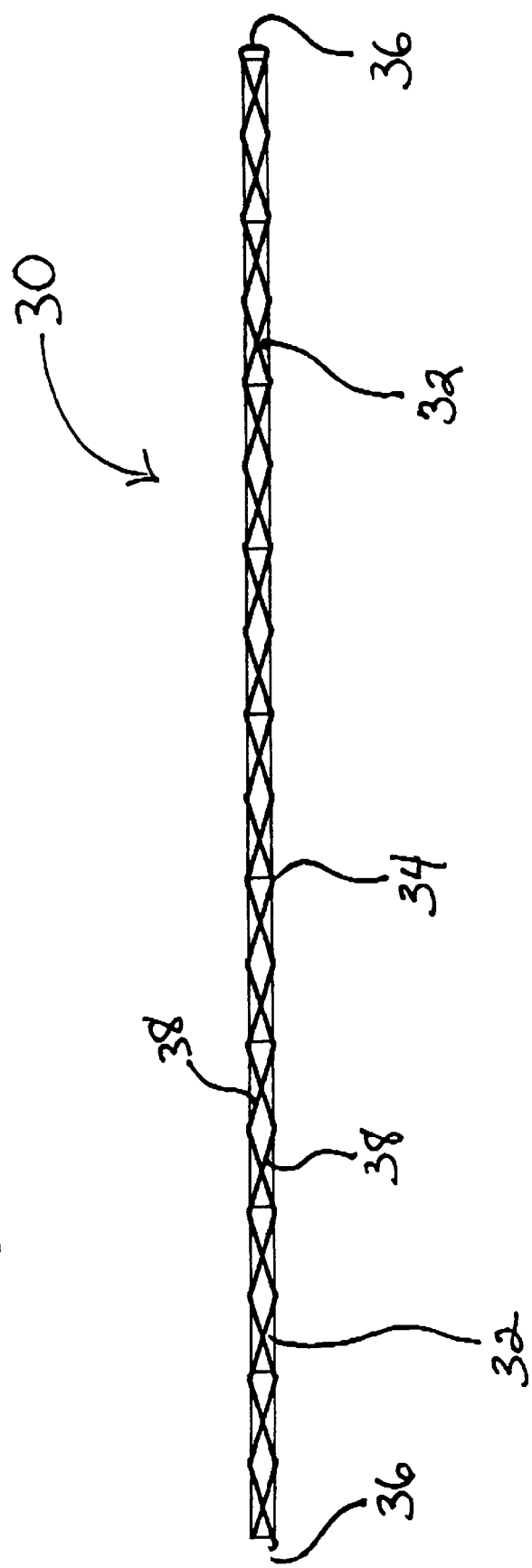
FIG. 6 shows a second embodiment of the jacket-enclosed radioactive source train of the present invention.

FIGS. 1–4 illustrate one embodiment of the radioactive source train 10 of the present invention. A series of individual radioactive source seeds or treating elements 12 are enclosed by a cylindrical sleeve or jacket 14 having a central elongated body portion fitted with end caps 16 at either end. The central elongated body portion has a proximal end, a distal end and a lumen extending therebetween and is formed of helically coiled wire 18 along its entire length. The cut away shown in FIG. 1 does not actually exist along the jacket 14 but rather is for visually showing the radioactive seeds 12 that lie within the enclosed jacket lumen. Although not shown, radiopaque marker seeds, which are visible under fluoroscopy, may also be a part of the radioactive source train 10. Such marker seeds may be non-radioactive and may be placed at either end of the series of radioactive seeds 12 to assist in the proper positioning of the radiation source train 10 at the targeted site for radiation exposure.

The helically coiled wire 18 is shown in FIGS. 1–2 as flat wire with a rectangular cross-section, also commonly referred to as ribbon wire, but can also be round wire with a circular cross-section, as seen in FIGS. 3–4, or wire of any other available cross-sectional shape. The pitch between coils can be large or small, depending on the preferred spacing between each coil and other differentiating characteristics, most importantly those that affect the movement of the jacket enclosed radioactive source train 10 through radii of curvature associated with the placement of a catheter. The coil pitch or spacing can be uniform, as seen in FIGS. 1–4, or can be variable along the length of the jacket 14, possibly for creating a jacket of variable stiffness.

One example of a source train jacket 20 with a variable coil pitch can be seen in FIG. 5. The coils 22 along each end of the jacket 20 are tightly wound to minimize or eliminate gaps between coils 22, while the coils 24 along the remainder of the jacket 20 between the two ends are of a greater pitch. The tightly wound coils 22 at either end of the jacket 20 provide more surface area for the attachment of the end caps 26 and can be used, in place of marker seeds, as markers for the proper placement of the jacketed source train 28 within the catheter. Wire 18 can be of a radiopaque material, which will enhance the visibility of the tightly coiled section under fluoroscopy. A variable coil pitch could also be used to form a jacket with variable stiffness along its length. Coils that have a large pitch produce greater gaps between each coil and thus, less coverage of the seeds along the length of the jacket. One advantage of having a large coil pitch may be the result of reduced shielding along the length of the radioactive seeds. Alternatively, less coil pitch may be warranted if shielding along the length of the radioactive seeds is desired to deliver the proper dose to the vascular wall. The coil pitch and its uniformity or variability may also be dictated by performance characteristics, such as sufficient flexibility that will allow for successful delivery and retrieval of the jacket-enclosed radioactive source train to and from a selected site via a pre-positioned catheter.

Figure 11:
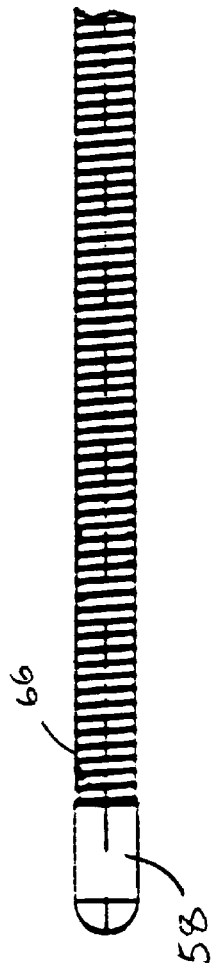
FIG. 11 shows a portion of a jacket-enclosed radioactive source train having a preferred end cap configuration.
Figure 12:
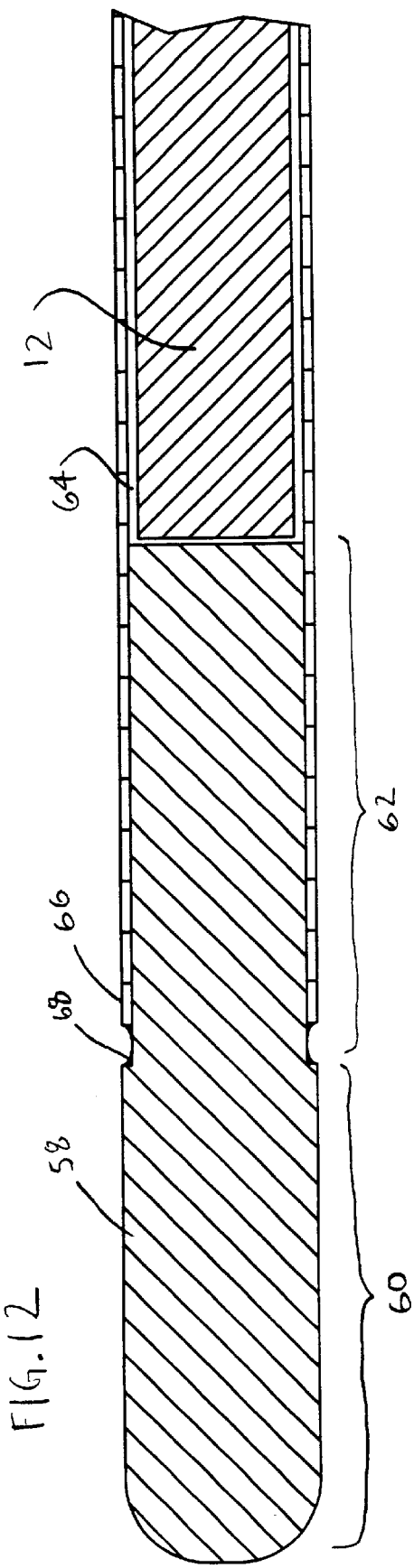
FIG. 12 is a partial longitudinal cross-section of the jacketed radioactive source train shown in FIG. 11.

To permanently enclose the treating elements an end cap 16, 26 is affixed, by, e.g., welding, gluing, soldering, brazing, solvent bonding or any acceptable method for joining metallic materials to each of the proximal and distal ends of the source train jacket 14, 20. A preferred end cap configuration can be seen in FIGS. 11 and 12. End cap 58 is an elongated cylinder and has first and second portions 60 and 62, the second portion 62 being of a slightly smaller outer diameter than the first end. The second portion 62 is sized to fit within the lumen 64 created by the coiled wire 66, while the first portion 60 is sized to be of the same outer diameter as the coiled wire 66 and remains outside the lumen 64 and adjacent to the coiled wire 66. A weld 68 along the intersection of portions 60 and 62 permanently affixes the end cap 58 to the coiled wire 66. There would, of course, be an identical end cap configuration at the other end of the jacket-enclosed radioactive source train, which is not displayed in FIGS. 11 and 12.

Alternatively, the wire can be affixed, for example by laser welding, to points along the radioactive seeds 12, and eliminating the need for end caps 16, 26.

FIG. 6 illustrates a second embodiment of the radioactive source train 30 of the present invention. A series of individual radioactive source seeds 32 are enclosed by a cylindrical sleeve or jacket 34 having a central elongated body portion fitted with end caps 36 at either end. The central elongated body portion has a proximal end, a distal end and a lumen extending therebetween and is formed of one or more wires 38 braided or intertwined along the entire length of the jacket body and gathered at the jacket ends before being fitted with end caps 36. End caps 36 are affixed, for example by gluing, welding, soldering, brazing, solvent bonding or any acceptable method for joining metallic materials to both ends of the elongated braided section. The end caps 36 can be formed at least partially from the wire ends remaining after the braided section is complete. Alternatively, as with the coiled wire embodiment, the braided wire or wires 38 can be affixed, for example by laser welding, to points along the radioactive seeds 12, and eliminating the need for end caps 36.

Each wire 38 can be flat, also referred to as ribbon wire, with a rectangular cross-section, round with a circular cross-section, or of any other available cross-sectional shape. The braided portion may be of any one or more patterns and may be tightly or loosely woven depending on the desired openness of the weave and the amount of desired flexibility. Also dependent on the desired flexibility of the source train jacket 34, the braided body portion may be of a uniform or varied construction along its entire length. A variable braid may also be formed where the tight pitch would act as the marker and the loose pitch would securely hold the radioactive seeds. Additionally, the braided wire or filaments can be configured to overlap the seeds 32 in a way so as to cover less surface area and thus, limiting any interference between the emitting radiation and the intended treatment site.

FIG. 7 illustrates a third embodiment of the radioactive source train 40 of the present invention. A series of individual radioactive source seeds 42 are enclosed by a sleeve or jacket 44, which is made of coiled or braided wire and which is attached to a push rod 46 to be used for maneuvering the jacketed radiation source train 40 to and from the intended treatment site. The jacket 44 has a central elongated body portion fitted with an end cap 48 at one or both ends. The central elongated body portion has a proximal end, a distal end and a lumen extending therebetween and can be formed of helically coiled wire, flat or round, or braided wires or filaments in any manner as described above with respect to the other embodiments disclosed herein. The push rod 46 is connected to one of the radioactive seeds 42 and/or the jacket 44. One end of the elongated body portion extends beyond the last of the series of radioactive seeds 42 and the push rod 44 is positioned within the coiled or braided extension so that it abuts the last of the series of radioactive seeds 42. The extended body portion is affixed, for example by welding, solvent bonding, or adhesives, to the body of the push rod 46. This embodiment is shown with only one end cap 48; however, the jacket 44 may be equipped with a second end cap to close the other end of the jacket 44, as shown in FIGS. 1–6. The push rod 46 could then be attached or fused to either of the two end caps.

The source train jackets 14, 34, 44 are comprised of materials that possess sufficient flexibility to give them the ability to travel smoothly through any radii of curvature they may encounter while traveling via a catheter to and from the targeted treatment site within the body of a patient. Metal, especially in wire form, is a good material choice; it will not degrade as a result of constant contact with radiation emitted from the radioactive source train. Some examples of metals include stainless steel, aluminum, alloys, and super elastic materials, such as nitinol. Radiopaque materials, such as gold, platinum, platinum iridium, tungsten, and tantalum can be used to create a source train jacket that is visible under fluoroscopy and assist in the proper alignment of the radioactive source train 10, 28, 30, 40 with the treatment site. The two ends of the source jacket are most crucial in assisting the placement of the radioactive source train. Thus, as an alternative, only the end caps 16, 26, 36, 48 are of a radiopaque material. Radiopaque materials are denser than those that are not radiopaque and may need to be avoided along the length of the source train so as not to dampen the radioactivity with its shielding effect. The push rod shown in FIG. 7 is also of sufficient flexibility and may be made of the same or similar materials as the source train jacket, but the best choices are likely to be stainless steel or a super elastic material. The length of the push rod is determined by the medical application and the specific location for radiotherapy within the body.

Wires 18, 22, 24, 38, 50 used in the formation of the source train jackets described above can be of any thickness, but preferably have a thickness in the range of 0.0005 inch to 0.0020 inch. This range allows for sufficient flexibility and does not significantly block the radiation so as to affect the radiation dose the treatment area receives from the radioactive source train 10, 28, 30, 40. The wire thickness also affects the overall diameter of the jacketed source train 10, 28, 30, 40, which in turn affects the diameter of the catheter source train lumen, which in turn affects the overall diameter of the catheter. Smaller catheters may be preferred for certain medical applications and larger catheters may be preferred for other medical applications. Any suitable width, of the flat or ribbon wire can be used, but preferably, the width is in the range of 0.002 inch to 0.005 inch. The wires 18, 22, 24, 38, 50 may also be coated to reduce the friction coefficient between the outer surface of the jacket 14, 20, 34, 44 and the inner surface of the catheter lumen in which it travels to and from the treatment site.

The radioactive source train 10, 28, 30, 40 can comprise any number of individual radioactive seeds 12, 32, 42 and each radioactive seed can be of any suitable length and diameter. Thus, the length and the diameter of the source train jacket 14, 20, 34, 44 are based upon the dimensions of and the number of individual radioactive seeds 12, 32, 42 and marker seeds. Additionally, the outer diameter of the source train is affected by the thickness of the wire 18, 22, 24, 38, 50 used to produce the coils or braids.

As shown in FIGS. 8–10, the jacket enclosed radiation source train 10 is positionable within a catheter lumen 50, 54 and is movable between the proximal and the distal end portions of the tube under motive force exerted by fluid flowing through the catheter lumens 50 and 52; 54 and 56.

For radiation exposure of the desired site, the radioactive seeds or treating elements contain radioactive material, preferably beta-emitting. In the preferred embodiment, the treating elements are elongated hollow cylinders which are preferably constructed of stainless steel, silver, titanium or other suitable material, and are ideally in the range of 2.0 to 5.5 mm in length. The cylindrical treating elements have rounded first and second ends with a chamber extending therebetween. The inner diameter of chamber is preferably in the range of 0.1 to 0.7 mm. A first end plug closes the first end of the cylinder, while a second end plug closes the second end. The end plugs are preferably less than about 1 mm in width and are affixed to cylinder, for example, by welding.

The outer diameter of the treating elements is preferably between approximately 0.3 and 0.8 mm, being sized, of course, to slidably fit into the respective receiving bores of the carriages, bodies and catheter lumens described above. To permit maximum mobility through the loading devices and catheters, the inner diameter of each of the bores or lumens the treating elements pass through should preferably be less than twice the outer diameter of the cylindrical treating elements. This allows the treating elements to move quickly through the lumen, minimizes unnecessary exposure of other tissue to the treating elements and in particular minimizes radiation exposure to other tissue.

Each treating element, as constructed above, encapsulates a therapeutic agent, such as radiation emitting substance. Radiation emitting substance is contained within interior chamber of the treating element and may be composed of any alpha, beta or gamma particle emitting substance. Preferably, however, the radioactive source is a pure beta-particle emitter, or beta and gamma emitter. Examples of such substances include Strontium 90, Yttrium-90, Ruthenium 106, Thulium-170, Tungstun-185, Phosphorus 32, Iridium 192, and/or Iodine 125.

The amount and strength of the radioactive material contained in the combined number of treating elements should be sufficient to deliver a desired dosage of from 100 to about 10,000 rads, preferably about 700 to 5000 rads, in about 1 to 10 minutes. Radioactivity is generally measured in units of "Curie" (Ci), and the radioactivity of the material for the present invention is selected to provide the above dosage. For the preferred dosage, the radioactive material may have a radioactivity of approximately 0.45 and 25,000 mCi per centimeter of vessel to be treated, depending on the radiation source used and the thickness of the materials between the source and the tissue to be treated. When the radioactive source train has dead space (non-radioactive) between adjacent elements, the train may be oscillated by moving the catheter slightly back and forth or by briefly repeatedly reversing the flow of fluid, resulting in a shifting back and forth of radiation source train to provide a more uniform radiation exposure of the selected area of the vessel.

The selected radioactive material may be contained within glass, foil, or ceramics, or alternatively, within a powder or liquid medium, such as microparticles in liquid suspension. Such radioactive materials may be formed into pellets, spheres, and/or rods in order to be placed into the chamber of the treating element.

Various alternative treating elements may also be used to contain the radioactive material without departing from the present invention. For example, the treating elements may be toroidal, spherical, or in the form of elongated rings or donuts, and in such configurations, the radioactive material may be actually impregnated in a metal and formed into the desired shape. Alternatively, a radioactive powder may be fired to fuse the material so that it may be formed into the desired shape, which may then be encapsulated in metal, such as titanium, stainless steel or silver, or in plastic, as by dipping in molten or uncured plastic. In still another embodiment, the treating elements may be formed from a ceramic material which has been dipped in a radioactive solution. In a still further alternative, the treating elements may be constructed in the form of two piece hollow cylindrical capsules having a larger diameter half with a central cavity and a smaller diameter half also having a central cavity, the smaller half slidably received within the larger half and bonded or welded to form the capsule structure.

The treating elements may comprise a radioactive material sintered into a ceramic rod, which is then encapsulated in a cylindrical stainless steel capsule. In practice, independent, non-connected treating elements are used in a series, with each element being approximately 2.5 mm in length so that the total length of the source train is 3 cm. However, the seed length and the number of seeds may vary so that the total length of the source train is equal to or longer than the length of the lesion to be treated. Such radioactive sources are dissolved within a solvent, such as chloride or sodium nitride into which a ceramic rod is dipped. The ceramic rod is then heated so as to sinter the radioactive material into the ceramic. The ceramic rod is then encapsulated within a hollow, stainless steel cylinder. Sharp edges are removed from the capsule, and a coating can be applied to the exterior surface so as to reduce the frictional coefficient associated with the capsule during delivery through the catheter. The walls of the cylinder may be sufficiently thick to block one type of radiation emitted from a particular radioactive source, while allowing a second type of radiation (a daughter element) to penetrate the cylinder.

As discussed previously, marker seeds can be positioned on either side of the radioactive seeds to assist in locating and positioning the radiation source train. The marker seeds may be made of radiopaque materials, such as gold, gold-plated stainless steel, synthetic ruby, platinum, platinum iridium, tungsten and tantalum, each of which can be seen under fluoroscopy.

The source train jacket 14, 20, 34, 44 and the radioactive seeds are combined together to form the jacket enclosed radioactive source train of the present invention. The elongated portion of the jacket 14, 20, 34, 44 is coiled or braided to a determined length and inner diameter. Then an end cap 16, 26, 36, 48 is affixed to one of the ends of the elongated coiled or braided portion, the radioactive seeds 12, 32, 42 and marker seeds, if used, are placed within the lumen of the jacket so they have end to end contact with one another, and the other end cap 16, 26, 36, 48 is affixed to the remaining open end of the jacket 14, 20, 34, 44.

The radioactive source train of the present invention may be introduced through a catheter into any one of the intraluminal passageways with the human body to treat the passageway or its surrounding areas. The diameter of the sources may vary so as to be appropriately sized with the catheter that will provide the optimal maneuverability within the chosen passageway (appropriate placement of the distal end of the catheter in relation to the treatment site).

Thus, a radioactive source train has been provided that accomplishes all the objects of the present invention. While the invention has been described in terms of certain preferred embodiments, there is no intent to limit it to the same. Instead, the scope of the invention is defined by the following claims.

What is claimed:

1. A treating element source train useable in a system for intraluminal treatment of a selected site in a body of a patient comprising:
    a plurality of treating elements, each treating element comprising a hollow outer housing closed on each end and a radiation-emitting substance encapsulated therein, the treating elements aligned end-to-end so as to have a proximal treating element on one end and a distal treating element on the other end; and
    a wire wound around the exterior of the treating elements to maintain the treating elements in their end-to-end relationship, said wire being secured to at least the proximal treating element and the distal treating element.

2. The treating element source train of claim 1 wherein the wire is helically coiled about the treating elements.

3. The treating element source train of claim 2 wherein the wire is secured to each treating element.

4. The treating element source train of claim 2 wherein the pitch of the helical coils is uniform along the length of the treating element source train.

5. The treating element source train of claim 2 wherein the pitch of the helical coils is varied along the length of the treating element source train so as to provide a variable stiffness.

6. The treating element source train of claim 2 wherein said wire is more tightly wound around the proximal treating element and the distal treating element than the treating elements therein between.

7. The treating element source train of claim 1 wherein the wire is braided around the treating elements.

8. The treating element source train of claim 7 wherein the wire is secured to each treating element.

9. The treating element source train of claim 2 or 3 wherein the wire is secured to the proximal and distal treating elements.

10. The treating element source train of claim 1 wherein the wire is made of radiopaque material.

11. The treating element source train of claim 10 wherein the wire is made of gold, platinum, platinum iridium, tungsten or tantalum.

12. The treating element source train of claim 1 wherein said wire is made of a material selected from the group consisting of stainless steel, aluminum and alloys thereof.

13. The treating element source train of claim 1 wherein said wire is made of a super elastic material.

14. The treating element source train of claim 13 wherein said super elastic material is nitinol.

15. The treating element source train of claim 1 wherein said radiation-emitting substance is a pure beta-emitting radioisotope.

16. A treating element source train useable in a system for intraluminal treatment of a selected site in a body of a patient comprising:
    a plurality of treating elements, each treating element comprising a hollow outer housing closed on each end and a radiation-emitting substance encapsulated therein, the treating elements aligned end-to-end so as to have a proximal treating element on one end and a distal treating element on the other end; and
    a wire wound around the exterior of the treating elements to maintain the treating elements in their end-to-end relationship;
    further comprising an end cap adjacent each of the proximal and distal treating elements, the wire being secured to each end cap.

17. The treating element source train of claim 16 wherein the end caps are made of a radiopaque material.

18. The treating element source train of claim 1 further comprising a push rod affixed to the wire adjacent the proximal treating element.

19. The treating element source train of claim 1 wherein the wire has a substantially flat cross-section.

20. The treating element source train of claim 1 wherein the wire has a circular cross-section.

21. The treating element source train of claim 1 wherein the wire includes a friction-reducing coating.

22. The treating element source train of claim 16 wherein said wire is tightly wound around the end caps and is wound with a greater pitch between said end caps.

* * * * *